(12) United States Patent
Drysdale et al.

(10) Patent No.: US 9,193,702 B2
(45) Date of Patent: Nov. 24, 2015

(54) FLUORINATED ARYL EPOXIDE COMPOUNDS

(71) Applicant: E I DU PONT DE NEMOURS AND COMPANY, Wilmington, DE (US)

(72) Inventors: Neville Everton Drysdale, Newark, DE (US); Garret D Figuly, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 86 days.

(21) Appl. No.: 14/068,930

(22) Filed: Oct. 31, 2013

(65) Prior Publication Data

US 2015/0119547 A1    Apr. 30, 2015

(51) Int. Cl.
*C07D 303/08* (2006.01)
*C07D 303/18* (2006.01)
*C07D 301/28* (2006.01)
*C08G 65/00* (2006.01)
*C07D 303/22* (2006.01)

(52) U.S. Cl.
CPC ............ *C07D 303/18* (2013.01); *C07D 301/28* (2013.01); *C07D 303/08* (2013.01); *C07D 303/22* (2013.01); *C08G 65/00* (2013.01)

(58) Field of Classification Search
None
See application file for complete search history.

(56) References Cited

U.S. PATENT DOCUMENTS

| | | | |
|---|---|---|---|
| 4,460,791 A | 7/1984 | Cooke | |
| 4,577,036 A | 3/1986 | Falk | |
| 4,876,018 A | 10/1989 | Karydas | |
| 5,198,570 A | 3/1993 | Feiring | |
| 5,643,495 A | 7/1997 | Bartmann et al. | |
| 5,646,222 A | 7/1997 | Maekawa et al. | |
| 7,531,700 B2 | 5/2009 | Petrov | |
| 8,962,879 B2 * | 2/2015 | Drysdale | 560/221 |
| 2006/0006364 A1 | 1/2006 | Shundo et al. | |
| 2007/0134440 A1 | 6/2007 | Kato | |
| 2011/0001088 A1 | 1/2011 | Ootsuki et al. | |
| 2012/0277460 A1 | 11/2012 | Percec et al. | |
| 2014/0135518 A1 * | 5/2014 | Drysdale | 560/8 |
| 2014/0135535 A1 * | 5/2014 | Drysdale | 568/593 |

FOREIGN PATENT DOCUMENTS

| | | |
|---|---|---|
| DE | 3828063 A1 | 2/1990 |
| DE | 4015681 A1 | 11/1991 |
| DE | 4015681 C2 | 11/1991 |
| EP | 0295813 A2 | 12/1988 |
| EP | 0355025 A2 | 8/1989 |
| EP | 0355025 A3 | 8/1989 |
| EP | 0391390 A1 | 10/1990 |
| EP | 0391390 B1 | 10/1990 |
| EP | 0610861 A1 | 8/1994 |
| EP | 0638629 A2 | 2/1995 |
| EP | 0638629 A3 | 2/1995 |
| EP | 0638629 B1 | 2/1995 |
| EP | 1036790 A1 | 9/2000 |
| EP | 1411104 A1 | 4/2004 |
| EP | 1411104 B1 | 5/2007 |
| GB | 1376315 A | 12/1974 |
| GB | 1404351 A | 8/1975 |
| GB | 2245587 A | 1/1992 |
| JP | 04159272 | 6/1992 |
| JP | 1994172266 A | 6/1994 |
| JP | 1997255608 A | 9/1997 |
| JP | 2006117564 A | 5/2006 |
| JP | 2006137856 A | 6/2006 |
| JP | 2011148761 A | 8/2011 |
| WO | 2007/149449 A2 | 12/2007 |
| WO | 2007/149449 A3 | 12/2007 |

OTHER PUBLICATIONS

CH3413WOPCT Search Report and Written Opinion, PCT/2013/069020 Dated Jan. 20, 2014.
CH3414WOPCT Search Report and Written Opinion, PCT/2013/069029 Dated Jan. 7, 2014.
CH3415WOPCT Search Report and Written Opinion, PCT/2013/069031 Dated Jan. 14, 2014.
IM1408WOPCT Search Report and Written Opinion, PCT/2014/062643 Dated Dec. 12, 2014.
Furin, G. et al. "Reaction of 1,1,2-trifluoro-2-hexaflouro-2'-(heptafluoropropoxy-propoxyethylene with amines or alcohols", Journal of Fluorine Chemistry, 106, (2000), pp. 13-14, XP002718135.
Dlouha, Ivine, Reactivity Study of 1,1,2,4,4,5,7,7,8,8,9,9,9-tridecafluoro-5-trifluoromethyl-3,6-dioxanon-1-ene in nucleophilic reactions: fluorination properties of secondary amine adducts, Journal Of Fluorine Chemistry, 117, (2002), pp. 149-159.

* cited by examiner

*Primary Examiner* — Robert Sellers

(57) ABSTRACT

A fluorinated aromatic epoxy compound having a fluorinated ether tail and a pendant epoxy functional group. These compounds are particularly useful as starting materials for producing various water and oil repellents and soil resists.

15 Claims, No Drawings

FLUORINATED ARYL EPOXIDE COMPOUNDS

FIELD OF THE INVENTION

The present invention relates to an aryl compound having a fluorinated ether group and a pendant epoxy group, useful for epoxy polymerization. The resulting polymers are useful for producing various water and oil repellents, soil resists, and surfactants.

BACKGROUND OF THE INVENTION

Water and oil repellants, soil resists, and surfactants are generally prepared from linear perfluorinated alcohols, which are expensive and are prepared through several step syntheses. These alcohols are either then reacted to make final products or further synthesized into intermediates prior to making final products. New starting materials are needed that do not utilize linear perfluorinated alcohols.

Compounds other than linear perfluorinated alcohols, more particularly non-linear compounds, are needed which can be used as starting materials and intermediates to produce compounds for water and oil repellents and soil resists. The present invention meets this need.

SUMMARY OF THE INVENTION

The present invention comprises a compound represented by Formula (I):

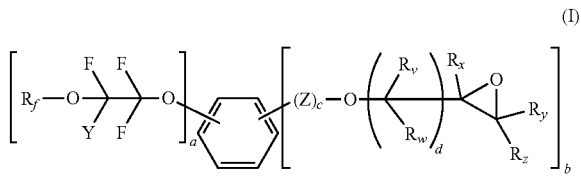

(I)

wherein
$R_f$ is —$CF_3$, —$C_2F_5$, or —$CF_2CFXCF_3$;
X is —F, or —$OC_3F_7$;
Y is —H, —Cl, or —Br;
each R is independently, —H, or $C_1$ to $C_{10}$ alkyl;
$R_v$ is —H, or $C_1$ to $C_{10}$ alkyl;
$R_w$ is —H, or $C_1$ to $C_{10}$ alkyl;
$R_x$ is —H, or $C_1$ to $C_{10}$ alkyl;
$R_y$ is —H, or $C_1$ to $C_{10}$ alkyl;
$R_z$ is —H, or $C_1$ to $C_{10}$ alkyl;
Z is independently selected from the group consisting of

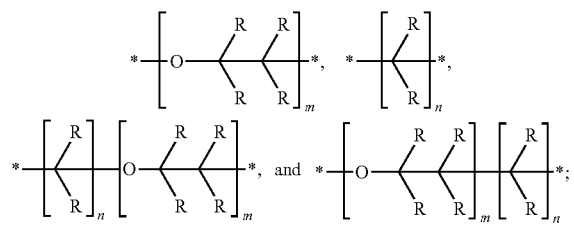

wherein each R is independently selected from —H or a $C_1$ to $C_{10}$ alkyl;
a is an integer from 1 to 5;
b is an integer from 1 to 5;
c is 0 or 1;
d is an integer from 1 to 10;
m is an integer from 1 to 10;
n is an integer from 1 to 10; and
* indicates a point of attachment.

The present invention also comprises a method of producing compounds of Formula (I):
comprising contacting a compound of Formula (XV)

(XV)

wherein
$R_1$ is —OH, —$(CR_2)_n$OH, —$(OCR_2CR_2)_m$OH, —$(CR_2)_n(OCR_2CR_2)_m$OH, —$(OCR_2CR_2)_m(CR_2)_n$OH
each R is independently, —H, or $C_1$ to $C_{10}$ alkyl;
a is an integer from 1 to 5;
b is an integer from 1 to 5;
m is an integer from 1 to 10;
n is an integer from 1 to 10
with one or more compounds of formula (XVI)

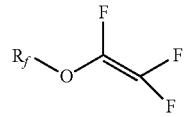

(XVI)

wherein
$R_f$ is —$CF_3$, —$C_2F_5$, or —$CF_2CFXCF_3$; and
X is —F, or —$OC_3F_7$.
in the presence of a base and a solvent having a donatable Y group wherein Y is H, Cl or Br, and
then contacting the resulting product with one or more compounds of formula (XXI):

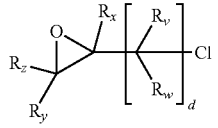

(XXI)

wherein
$R_v$ is —H, or $C_1$ to $C_{10}$ alkyl;
$R_w$ is —H, or $C_1$ to $C_{10}$ alkyl;
$R_x$ is —H, or $C_1$ to $C_{10}$ alkyl;
$R_y$ is —H, or $C_1$ to $C_{10}$ alkyl;
$R_z$ is —H, or $C_1$ to $C_{10}$ alkyl; and
d is an integer from 1 to 10
in the presence of an aqueous base in aqueous solution and a catalyst.

The present invention also relates to a polymer made from the compound of formula (I), and applications thereof.

DETAILED DESCRIPTION OF THE PREFERRED EMBODIMENTS

Herein trademarks are shown in upper case.

The present invention provides fluorinated aryl epoxide compound(s), and more particularly an aryl compound having a fluorinated ether group and a pendant epoxy group, a polymer of the compound, and applications thereof. The compound, in particular, is useful as a starting monomer to produce polymers for water and oil repellents and soil resists. The compound is also, sometimes referred to herein as a fluorinated aromatic epoxide compound.

Reference will now be made in detail to the preferred embodiments of the invention. The invention may, however, be embodied in many different forms and should not be construed as limited to the embodiments set forth herein.

The present invention provides a compound of formula (I)

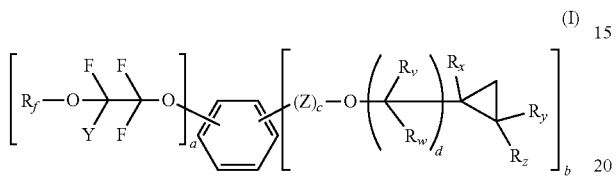

wherein
$R_f$ is —$CF_3$, —$C_2F_5$, or —$CF_2CFXCF_3$;
X is —F, or —$OC_3F_7$;
Y is —H, —Cl, or —Br;
each R is independently selected from —H, or $C_1$ to $C_{10}$ alkyl;
$R_v$ is —H, or $C_1$ to $C_{10}$ alkyl;
$R_w$ is —H, or $C_1$ to $C_{10}$ alkyl;
$R_x$ is —H, or $C_1$ to $C_{10}$ alkyl;
$R_y$ is —H, or $C_1$ to $C_{10}$ alkyl;
$R_z$ is —H, or $C_1$ to $C_{10}$ alkyl;
Z is selected from the group consisting of

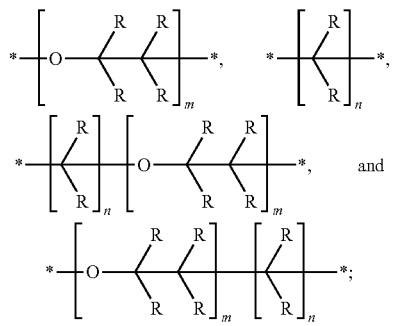

wherein each R is independently selected from —H or a $C_1$ to $C_{10}$ alkyl;
a is an integer from 1 to 5;
b is an integer from 1 to 5;
c is 0 or 1;
d is an integer from 1 to 10;
m is an integer from 1 to 10;
n is an integer from 1 to 10; and
* indicates a point of attachment.

Compounds of the present invention include pendent (or side) groups ($R_f$—O—CFY—$CF_2$O—)$_a$ and

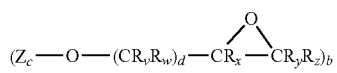

and wherein a is 1 to 5 and b is 1 to 5. Compounds of the present invention may have 1, 2, 3, 4 or 5 pendent groups of $R_f$—O—CFY—$CF_2$O—, and 1, 2, 3, 4 or 5 pendent groups of

and mixtures thereof, provided that the total number of pendent groups is less than or equal to 6. The $R_f$—O—CFY—$CF_2$O— and

groups may be ortho, para, or meta on the benzene ring or combinations thereof. In addition, when c is 0 in Formula (I), Z is not present, or in other words, as will be appreciated by one of skill in the art, Z is a single bond. It should also be understood that for all alkyl substituents listed in formula (I) and in other formulas described herein, the $C_1$ to $C_{10}$ alkyl group can be either a straight or branched chain alkyl group. It should also be understood that $R_v$, $R_w$, $R_x$, $R_y$, and $R_z$ are each independently selected from —H, or $C_1$ to $C_{10}$ alkyl in Formula (I).

Some embodiments of compounds of Formula (I) include those where $R_f$ is —$CF_3$, —$C_2F_5$, —$CF_2CFXCF_3$; X is —F, or —$OC_3F_7$; Y is —H, —Cl, or —Br, Z is —$(CR_2)_nO$, —$(OCR_2CR_2)_mO$, wherein each of m and n are independently 1, 2, 3, 4, 5, or 6. More preferred are compounds of Formula (I) wherein Z is —$(CH_2)_nO$, —$(OCH_2CH_2)_mO$, and —$(CH_2)_n(OCH_2CH_2)_mO$, wherein each of m and n are independently 1, 2, or 3. Also, other embodiments are those wherein $R_f$ is —$CF_3$ or —$C_2F_5$, and each R is —H or $C_1$ to $C_{10}$ alkyl, and $R_v$, $R_w$, $R_x$, $R_y$, $R_z$ are H, wherein each of m and n are independently 1, 2, or 3.

Additional embodiments of Formula (I) are those wherein R is an alkyl of 1, 2, 3, 4, 5, or 6 carbons; and $R_v$, $R_w$, $R_x$, $R_y$, $R_z$ are H. More preferred are compounds of those of Formula (I) listed below and those made in the examples provided herein.

In some embodiments, the compound of the present invention has Formula (II):

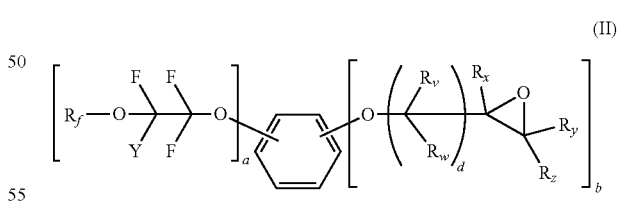

wherein:
$R_f$ is —$CF_3$, —$C_2F_5$, or —$CF_2CFXCF_3$;
X is —F, or —$OC_3F_7$;
Y is —H, —Cl, or —Br;
each R is independently selected from —H, or $C_1$ to $C_{10}$ alkyl;
$R_v$ is —H, or $C_1$ to $C_{10}$ alkyl;
$R_w$ is —H, or $C_1$ to $C_{10}$ alkyl;
$R_x$ is —H, or $C_1$ to $C_{10}$ alkyl;
$R_y$ is —H, or $C_1$ to $C_{10}$ alkyl;
$R_z$ is —H, or $C_1$ to $C_{10}$ alkyl;

a is an integer from 1 to 5;
b is an integer from 1 to 5; and
d is an integer from 1 to 10.

In some embodiments, the compound of the present invention has Formula (III):

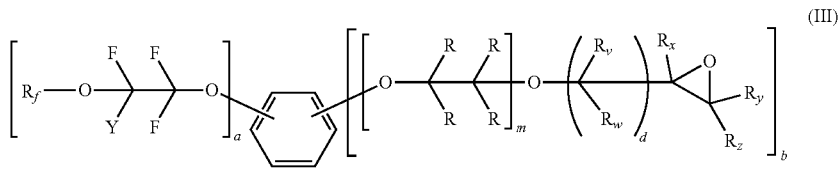

(III)

wherein:
$R_f$ is —$CF_3$, —$C_2F_5$, or —$CF_2CFXCF_3$;
X is —F, or —$OC_3F_7$;
Y is —H, —Cl, or —Br;
each R is independently selected from —H, or $C_1$ to $C_{10}$ alkyl;
$R_v$ is —H, or $C_1$ to $C_{10}$ alkyl;
$R_w$ is —H, or $C_1$ to $C_{10}$ alkyl;
$R_x$ is —H, or $C_1$ to $C_{10}$ alkyl;
$R_y$ is —H, or $C_1$ to $C_{10}$ alkyl;
$R_z$ is —H, or $C_1$ to $C_{10}$ alkyl;
a is an integer from 1 to 5;
b is an integer from 1 to 5;
d is an integer from 1 to 10; and
m is an integer from 1 to 10.

In some embodiments, the compound of the present invention has Formula (IV):
wherein:

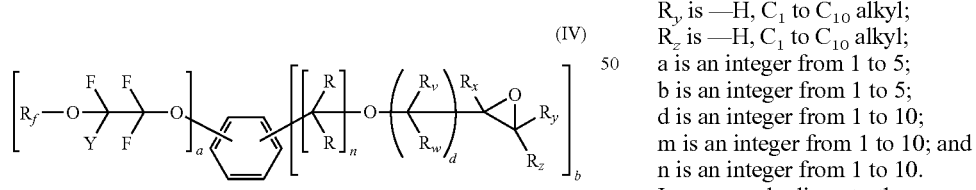

(IV)

$R_f$ is —$CF_3$, —$C_2F_5$, or —$CF_2CFXCF_3$;
X is —F, or —$OC_3F_7$;
Y is —H, —Cl, or —Br;
each R is independently selected from —H, or $C_1$ to $C_{10}$ alkyl;
$R_v$ is —H, or $C_1$ to $C_{10}$ alkyl;
$R_w$ is —H, or $C_1$ to $C_{10}$ alkyl;
$R_x$ is —H, $C_1$ to $C_{10}$ alkyl;
$R_y$ is —H, $C_1$ to $C_{10}$ alkyl;
$R_z$ is —H, $C_1$ to $C_{10}$ alkyl;
a is an integer from 1 to 5;
b is an integer from 1 to 5;
d is an integer from 1 to 10; and
n is an integer from 1 to 10.

In some embodiments, the compound of the present invention has Formula (V):

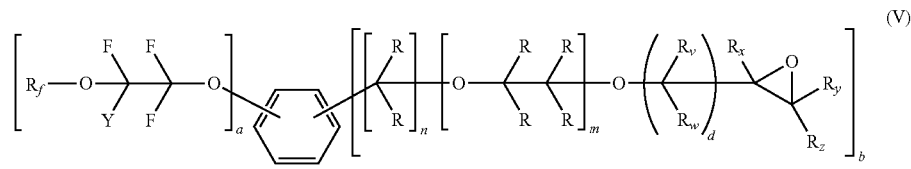

(V)

wherein:
$R_f$ is —$CF_3$, —$C_2F_5$, or —$CF_2CFXCF_3$;
X is —F, or —$OC_3F_7$;
Y is —H, —Cl, or —Br;
each R is independently selected from —H, or $C_1$ to $C_{10}$ alkyl;
$R_v$ is —H, or $C_1$ to $C_{10}$ alkyl;
$R_w$ is —H, or $C_1$ to $C_{10}$ alkyl;
$R_x$ is —H, $C_1$ to $C_{10}$ alkyl;
$R_y$ is —H, $C_1$ to $C_{10}$ alkyl;
$R_z$ is —H, $C_1$ to $C_{10}$ alkyl;
a is an integer from 1 to 5;
b is an integer from 1 to 5;
d is an integer from 1 to 10;
m is an integer from 1 to 10; and
n is an integer from 1 to 10.

In some embodiments, the compound of the present invention has Formula (VI):

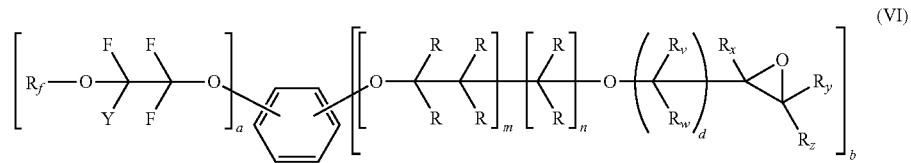

(VI)

wherein:
$R_f$ is —$CF_3$, —$C_2F_5$, or —$CF_2CFXCF_3$;
X is —F, or —$OC_3F_7$;
Y is —H, —Cl, or —Br;
each R is independently selected from —H, or $C_1$ to $C_{10}$ alkyl;
$R_v$ is —H, or $C_1$ to $C_{10}$ alkyl;
$R_w$ is —H, or $C_1$ to $C_{10}$ alkyl;
$R_x$ is —H, $C_1$ to $C_{10}$ alkyl;
$R_y$ is —H, $C_1$ to $C_{10}$ alkyl;
$R_z$ is —H, $C_1$ to $C_{10}$ alkyl;
a is an integer from 1 to 5;
b is an integer from 1 to 5;
d is an integer from 1 to 10;
m is an integer from 1 to 10; and
n is an integer from 1 to 10.

In some embodiments, the compound has Formula VII

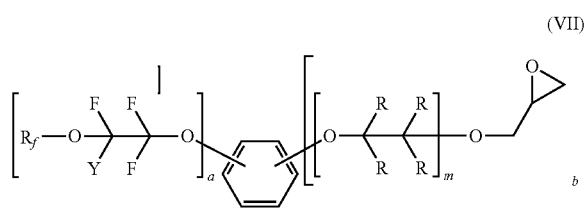
(VII)

wherein:
$R_f$ is —$CF_3$, —$C_2F_5$, or —$CF_2CFXCF_3$;
X is —F, or —$OC_3F_7$;
Y is —H, —Cl, or —Br;
each R is independently selected from —H, or $C_1$ to $C_{10}$ alkyl;
a is an integer from 1 to 5;
b is an integer from 1 to 5; and
m is an integer from 1 to 10.

In some embodiments, the compound has Formula VIII

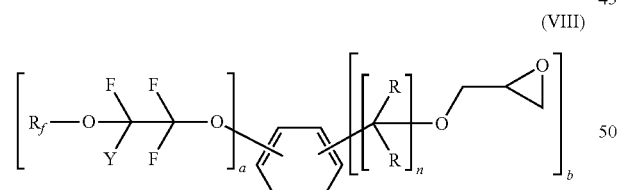
(VIII)

wherein:
$R_f$ is —$CF_3$, —$C_2F_5$, or —$CF_2CFXCF_3$;
X is —F, or —$OC_3F_7$;
Y is —H, —Cl, or —Br;
each R is independently selected from —H, or $C_1$ to $C_{10}$ alkyl;
a is an integer from 1 to 5;
b is an integer from 1 to 5; and
n is an integer from 1 to 10.

Preferred specific examples of compounds of Formula (I) include but are not limited to, the following six compounds.

A compound represented by Formula IX:

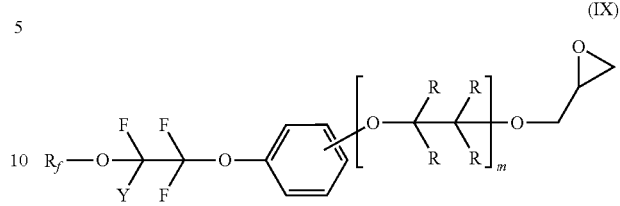
(IX)

wherein R, $R_f$, Y, and m are as defined above in Formula (I), and

A compound represented by Formula X:

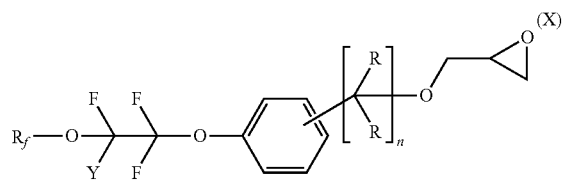
(X)

wherein R, $R_f$, Y, and n are as defined above in Formula (I).

A compound represented by formula XI:

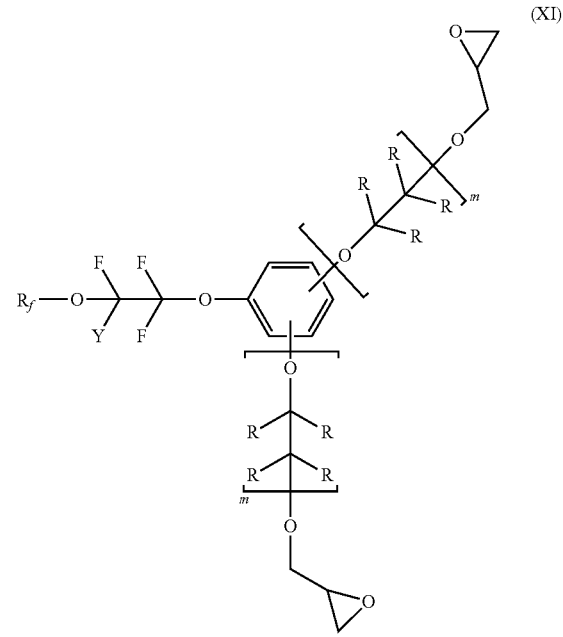
(XI)

wherein R, $R_f$, Y, and m are as defined above in Formula (I), and wherein the two pendant epoxy groups may be located at any of the positions on the benzene ring not occupied by the fluoro substitutent.

A compound represented by formula XII:

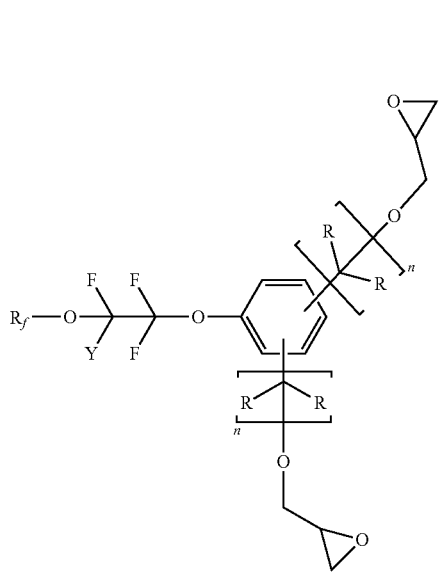

wherein R, $R_f$, Y, and n are as defined above in Formula (I), and wherein the two pendant epoxy groups may be located at any of the positions on the benzene ring not occupied by the fluoro substitutent.

A compound represented by formula XIII:

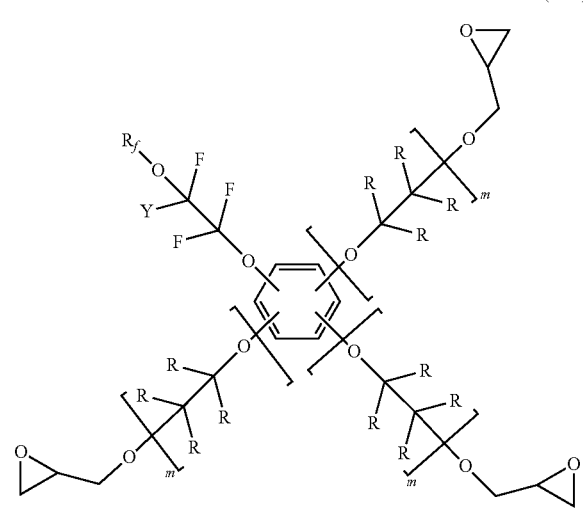

wherein R, $R_f$, Y, and m are as defined above in Formula (I), and wherein the three pendant epoxy groups may be located at any of the positions on the benzene ring not occupied by the fluoro substitutent.

A compound represented by formula XIV:

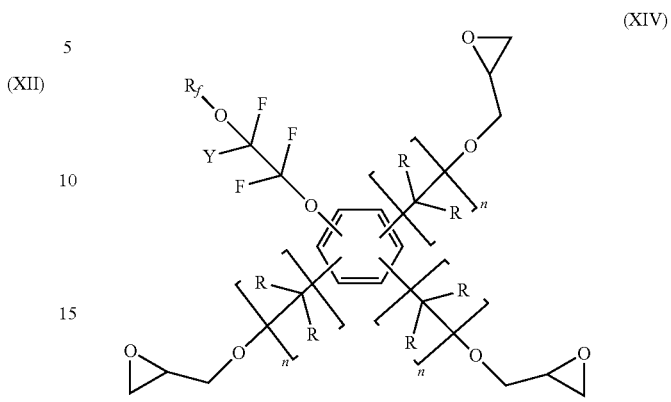

wherein R, $R_f$, Y, and n are as defined above in Formula (I), and wherein the three pendant epoxy groups may be located at any of the positions on the benzene ring not occupied by the fluoro substitutent.

The present invention also provides a polymer obtained by reacting the epoxy groups of at least one of the monomers as described in any of Formulas (I) to (XIV) above, with at least one other polymerizable monomer which contains at least one group reactive with the epoxy groups. The polymerizable monomer can be either the same compound or different compound selected from any of compounds described in Formulas (I) to (XIV) above, or can be another type of polymerizable material such as one selected from the group consisting of bisphenol diglycidyl ethers, epoxy novalacs, and curing agents such as mono-, di- and tri-functional amines, and the like.

Compounds of Formulas (I) to (XIV) can be produced in various ways.

In one embodiment, compounds of the present invention of Formula (I) can be prepared by contacting a variety of functionalized aryl rings of Formula (XXI)

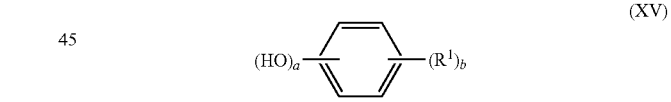

wherein $R^1$ is —OH, —$(CR_2)_n$OH, —$(OCR_2CR_2)_m$OH, —$(CR_2)_n(OCR_2CR_2)_m$OH, —$(OCR_2CR_2)_m(CR_2)_n$OH; n is 1 to 10; m is 1 to 10; R is $C_1$ to $C_{10}$ alkyl; R is independently, —H, or $C_1$ to $C_{10}$ alkyl; a is an integer from 1 to 5; b is an integer from 1 to 5;

with one or more perfluorovinyl ethers of formula (XVI)

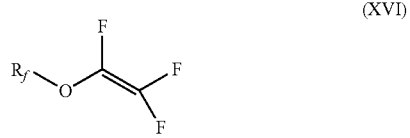

wherein $R_f$ is —$CF_3$, —$C_2F_5$, or —$CF_2CFXCF_3$; and X is —F, or —$OC_3F_7$.

For compounds of Formula (XIV), when $R_f$ is —$CF_3$, the compound is perfluoromethylvinyl ether of Formula (XVII)

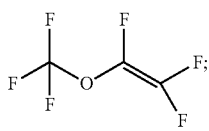
(XVII)

when $R_f$ is —$C_2F_5$, the compound is a perfluorovinyl ethyl ether of Formula (XVIII)

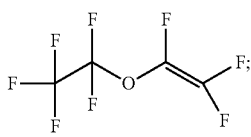
(XVIII)

when $R_f$ is —$CF_2CFXCF_3$ and X is —F, the compound is a perfluoropropylvinyl ether of Formula (XIX)

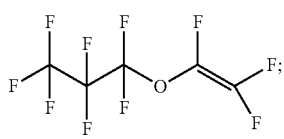
(XIX)

and when $R_f$ is —$CF_2CFXCF_3$ and X is —$OC_3F_7$, the compound is a perfluoropropylvinyl ether of Formula (XX)

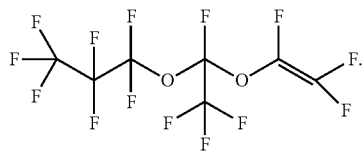
(XX)

The reaction of the aryl compounds of Formula (XV) with perfluorovinyl ethers of Formula (XVI) can be completed in a solvent and a base. Suitable bases include those known to deprotonate the hydrogen of a phenol. Examples of such bases include, but are not limited to, potassium carbonate, sodium carbonate, and potassium bicarbonate. Examples of suitable solvents include, but are not limited to, tetrahydrofuran, carbon tetrachloride, and carbon tetrabromide. In Formula (I), when tetrahydrofuran is the solvent, then Y is —H. In Formula (I), when carbon tetrachloride is the solvent, then Y is —Cl. In Formula (I), when carbon tetrabromide is the solvent, then Y is —Br. The reaction can be conducted between room temperature and solvent reflux temperatures. The phenolic hydroxyl group is more reactive with the perfluorinated vinyl ether such that the fluoro group will react with only one side of the benzyl alcohol.

The resulting perfluorinated aromatic alcohol can then be contacted with one or more compounds of formula (XXI) (i.e., with epichlorohydrin, substituted epichlorohydrin, or mixtures thereof):

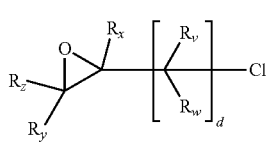
(XXI)

wherein
$R_v$ is —H, or $C_1$ to $C_{10}$ alkyl;
$R_w$ is —H, or $C_1$ to $C_{10}$ alkyl;
$R_x$ is —H, or $C_1$ to $C_{10}$ alkyl;
$R_y$ is —H, or $C_1$ to $C_{10}$ alkyl;
$R_1$ is —H, or $C_1$ to $C_{10}$ alkyl; and
d is an integer from 1 to 10
in the presence of aqueous base in aqueous solution and a catalyst to complete the reaction and produce the desired compounds of Formulas (I) to (XIV). Epichlorohydrin is especially preferred in this step of the reaction which is represented by the above formula where $R_v$, $R_w$, $R_x$, $R_y$, and $R_z$ are all H and d is 1, as shown below in formula XXII

(XXII)

Examples of suitable bases include, but are not limited to, sodium hydroxide, potassium hydroxide, potassium carbonate and other bases known to one skilled in the art. Examples of suitable catalysts which are used in a catalytically effective amount, include, but are not limited to, tetrabutylammonium sulfate, tetramethylammonium chloride and other phase transfer catalysts known to one skilled in the art.

Compounds of the present invention and as defined above, are useful, for example, as starting monomers and intermediates for producing polymers for water and oil repellents and soil resists.

The invention will now be further clarified by consideration of the following examples which are intended to be purely exemplary and are not intended, nor should they be interpreted to, limit the scope of the invention.

EXAMPLES

Materials

Perfluorovinyl ethers 1,1,1,2,2,3,3-heptafluoro-3-((1,2,2-trifluorovinyl)oxy)propane and 1,1,1,2,2,3,3-heptafluoro-3-(1,1,1,2,3,3-hexafluoro-3-(1,2,2-trifluorovinyloxy)propan-2-yloxy)propane are commercially available from E. I. du Pont de Nemours and Company, Wilmington, Del. All other reactants, unless otherwise specified, are available from Sigma-Aldrich, St. Louis, Mo.

Example 1

Preparation of (2-((2-(2-(1,1,2-trifluoro-2-(perfluoropropoxy)ethoxy)phenoxy)ethoxy)methyl)oxirane)

The above named compound was synthesized in the following manner using a two-step synthesis process.
Synthesis Step (1)
The compound shown below was synthesized in the following manner:

2-(2-(1,1,2-trifluoro-2-(perfluoropropoxy)ethoxy)phenoxy) ethanol

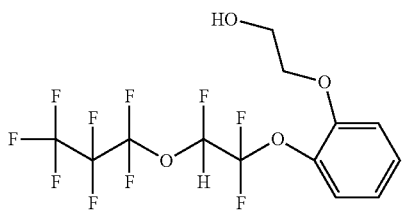 [SMILES: OCCOc1ccccc1OC(F)(F)C(F)OC(F)(F)C(F)(F)C(F)(F)F]

In the dry box, tetrahydrofuran (2000 mL) and 2-(hydroxyethoxy)phenol (30.8 g, 0.20 mol) were added to a round bottom flask equipped with a stirrer. Potassium carbonate (13.8 g, 0.10 mol) was then added to the flask. 1,1,1,2,2,3,3-heptafluoro-3-((1,2,2-trifluorovinyl)oxy)propane (79.89 g, 0.30 mol) was then added via the addition funnel and the reaction was placed in an oil bath and heated to a gentle reflux overnight. The content was analyzed by proton NMR to be 2-(2-(1,1,2-trifluoro-2-(perfluoropropoxy)ethoxy)phenoxy) ethanol. The potassium carbonate was removed via filtration and the resulting material concentrated via roto-evaporation. Vacuum distillation afforded the desired material, bp 96-97° C. at 1.0-1.2 torr, 94.8% yield).

Synthesis Step (2)

The desired compound shown below was then synthesized from the compound produced above in Synthesis Step (1): (2-((2-(2-(1,1,2-trifluoro-2-(perfluoropropoxy)ethoxy)phenoxy)ethoxy)methyl)oxirane)

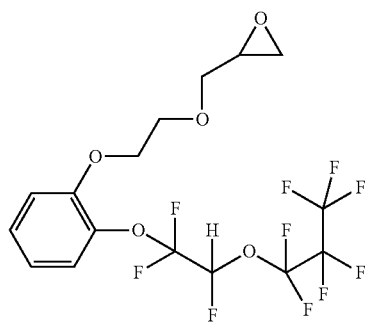 [SMILES: FC(OC(F)(F)C(F)(F)C(F)(F)F)C(F)(F)Oc1ccccc1OCCOCC1CO1]

In a three neck round bottom flask equipped with a magnetic stirring bar was added 50 wt % NaOH (20.00 mL) and tetrabutyl ammonium hydrogen sulfate (0.48 g). The resulting mixture was cooled to below 10° C. with an ice bath and epichlorohydrin (15.00 mL) was added. To this cooled solution was added 2-(2-(1,1,2-trifluoro-2-(perfluoropropoxy) ethoxy)phenoxy)ethanol (11.00 g) (from Synthesis Step 1 of Example 1) via a pressure equalizing addition funnel, keeping the temperature below 10° C. After completion the reaction mixture was allowed to warm to room temperature and stirred at this temperature for two hours. The content was poured into a mixture of ice and water (~100 g each) and the organic was extracted with methylene chloride (2×150 mL). The combined organic phase was washed with water and then dried over anhydrous sodium sulfate. The sodium sulfate was filtered off and the remaining organic phase was concentrated at reduced pressure and then fractionally vacuum distilled.

| Fraction | Head Temp (° C.) | Pot Temp. (° C.) | Vac. (torr) | Wt. (g) |
|---|---|---|---|---|
| 1 | 51-108 | 140-155 | 0.95 | 1.60 |
| 2 | 108-119 | 155 | 0.95 | 4.10 |
| 3. | 119-121 | 155-175 | 0.95 | 1.57 |
| 4 | 121-123.5 | 175 | 0.95 | 12.73 |

The content of the fractions was anaylzed by NMRs (Proton, Carbon and Fluorine) which showed Fraction 4 to be the desired material.

Example 2

Preparation of 2-(((4-(1,1,2-trifluoro-2-(perfluoropropoxy)ethoxy)benzyl)oxy)methyl)oxirane The above named compound was synthesized in the following manner using a two-step synthesis process.

Synthesis Step (1)

The compound shown below was synthesized in the following manner:
(4-(1,1,2-trifluoro-2-(perfluoropropoxy)ethoxy)phenyl) methanol

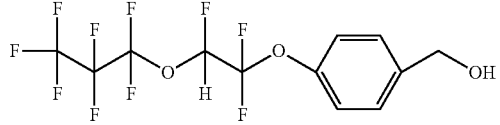 [SMILES: OCc1ccc(OC(F)(F)C(F)OC(F)(F)C(F)(F)C(F)(F)F)cc1]

In the dry box, tetrahydrofuran (2000 mL) and 4-(hydroxymethyl)phenol (24.8 g, 0.20 mol) were added to a round bottom flask equipped with a stirrer. Potassium carbonate (13.8 g, 0.10 mol) was then added to the flask. 1,1,1,2,2,3,3-heptafluoro-3-((1,2,2-trifluorovinyl)oxy)propane (79.89 g, 0.30 mol) was then added via the addition funnel and the reaction was placed in an oil bath and heated to a gentle reflux overnight. The content was analyzed by proton NMR to be (4-(1,1,2-trifluoro-2-(perfluoropropoxy)ethoxy)phenyl) methanol. The potassium carbonate was removed via filtration and the resulting material concentrated via roto-evaporation. Vacuum distillation afforded the desired material, bp 89-92° C. at 1.00 torr, 87.6% yield).

Synthesis Step (2)

The desired compound shown below was synthesized from the compound produced above in Synthesis Step (1): 2-(((4-(1,1,2-trifluoro-2-(perfluoropropoxy)ethoxy)benzyl) oxy)methyl)oxirane

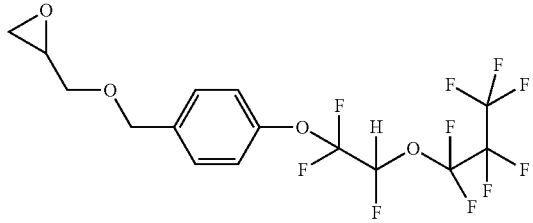 [SMILES: FC(OC(F)(F)C(F)(F)C(F)(F)F)C(F)(F)Oc1ccc(COCC2CO2)cc1]

In a 500 mL three neck round bottom flask equipped with a mechanical stirrer was added 50 wt % NaOH (80.00 mL) and tetrabutyl ammonium hydrogen sulfate (2.00 g). The resulting mixture was cooled to below 10° C. with an ice bath and epichlorohydrin (60.00 mL) was added. To this cooled solution was added (4-(1,1,2-trifluoro-2-(perfluoropropoxy) ethoxy)phenyl)methanol (44.00 g) (from Synthesis Step 1 of Example 2) via a pressure equalizing addition funnel, keeping the temperature below 10° C. After completion the reaction mixture was allowed to warm to room temperature and stirred at this temperature over-night. The content was poured into a mixture of ice and water (~400 g each) and the organic was extracted with methylene chloride (2×400 mL). The combined organic phase was washed with water and then dried over anhydrous sodium sulfate. The sodium sulfate was filtered off and the remaining organic phase was concentrated at reduced pressure and then fractionally vacuum distilled.

| Fraction | Head Temp (° C.) | Pot Temp. (° C.) | Vac. (torr) | Wt. (g) |
|---|---|---|---|---|
| 1 | 50-107 | 140 | 1.10 | — |
| 2 | 107-108 | 140 | 0.90-1.00 | 7.40 |
| 3. | 108-109 | 140 | 1.00 | 1.80 |
| 4 | 109-116 | 140-160 | 1.00-1.10 | 38.4 |

The content of the fractions was anaylzed by NMRs (Proton, Carbon and Fluorine) which showed Fraction 4 to be the desired material, which represents a yield of 76.3%.

Example 3

Preparation of 2-(((4-(1,1,2-trifluoro-2-(1,1,2,3,3,3-hexafluoro-2-(perfluoropropoxy)propoxy)ethoxy)benzyl)oxy)methyl)oxirane The above named compound was synthesized in the following manner using a two-step synthesis process.

Synthesis Step (1)

The compound shown below was synthesized in the following manner:
(4-(1,1,2-trifluoro-2-(1,1,2,3,3,3-hexafluoro-2-(perfluoropropoxy)propoxy)ethoxy)phenyl)methanol

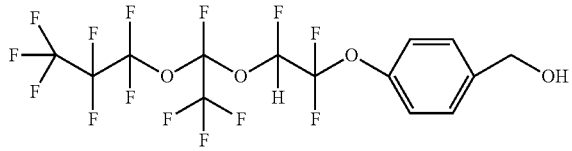 [SMILES: OCc1ccc(OC(F)(F)C(F)OC(F)(OC(F)(F)C(F)(F)C(F)(F)F)C(F)(F)F)cc1]

In the dry box, tetrahydrofuran (50 mL) and 4-(hydroxymethyl)phenol (0.62 g, 0.005 mol) were added to a round bottom flask equipped with a stirrer. Potassium carbonate (0.345 g, 0.0025 mol) was then added to the flask. 1,1,1,2,2,3,3-Heptafluoro-3-(1,1,1,2,3,3-hexafluoro-3-(1,2,2-trifluorovinyloxy)propan-2-yloxy)propane (3.24 g, 0.0075 mol) was then added via the addition funnel and the reaction was placed in an oil bath and heated to a gentle reflux over 2 days. The content was analyzed by proton NMR and shown to be (4-(1, 1,2-trifluoro-2-(1,1,2,3,3,3-hexafluoro-2-(perfluoropropoxy)propoxy)ethoxy)phenyl)methanol.

Synthesis Step (2)

The desired compound shown below was then synthesized from the compound produced above in Synthesis Step (1):
2-(((4-(1,1,2-trifluoro-2-(1,1,2,3,3,3-hexafluoro-2-(perfluoropropoxy)propoxy)ethoxy)benzyl)oxy)methyl)oxirane

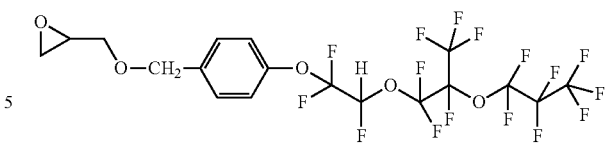

In a three neck round bottom flask equipped with a magnetic stirring bar was added 50 wt % NaOH (25.00 mL) and tetrabutyl ammonium hydrogen sulfate (0.50 g). The resulting mixture was cooled to below 10° C. with an ice bath and epichlorohydrin (15.00 mL0) was added. To this cooled solution was added (4-(1,1,2-trifluoro-2-(1,1,2,3,3,3-hexafluoro-2-(perfluoropropoxy)propoxy)ethoxy)phenyl)methanol (15.00 g) (from Synthesis Step 1 of Example 3) via a pressure equalizing addition funnel, keeping the temperature below 10° C. After completion the reaction mixture was allowed to warm to room temperature and stirred at this temperature for two hours. The content was poured into a mixture of ice and water (~100 g each) and the organic was extracted with methylene chloride (2×150 mL). The combined organic phase was washed with water and then dried over anhydrous sodium sulfate. The sodium sulfate was filtered off and the remaining organic phase was concentrated at reduced pressure and then fractionally vacuum distilled.

| Fraction | Head Temp (° C.) | Pot Temp. (° C.) | Vac. (torr) | Wt. (g) |
|---|---|---|---|---|
| 1 | <120 | 170 | 1.00 | — |
| 2 | 120-122 | 180 | 1.00 | 2.00 |
| 3. | 122-123 | 180 | 1.00 | 0.70 |
| 4 | 123-124 | 180-190 | 1.00 | 9.80 |

The content of the fractions was analyzed by NMRs (Proton, Carbon and Fluorine) which showed Fraction 4 to be the desired material.

Various other modifications, alterations, additions or substitutions of the compounds and compositions of this invention will be apparent to those skilled in the art without departing from the spirit and scope of this invention. This invention is not limited by the illustrative embodiments set forth herein, but rather is defined by the following claims.

What is claimed is:
1. A compound represented by the following Formula (I):

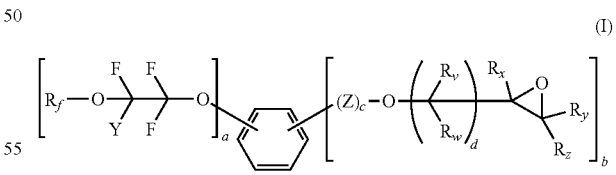

wherein
$R_f$ is —$CF_3$, —$C_2F_5$, or —$CF_2CFXCF_3$;
X is —F, or —$OC_3F_7$;
Y is —H, —Cl, or —Br;
each R is independently, —H, or $C_1$ to $C_{10}$ alkyl;
$R_v$ is —H, or $C_1$ to $C_{10}$ alkyl;
$R_w$ is —H, or $C_1$ to $C_{10}$ alkyl;
$R_x$ is —H, $C_1$ to $C_{10}$ alkyl;
$R_y$ is —H, $C_1$ to $C_{10}$ alkyl;
$R_z$ is —H, $C_1$ to $C_{10}$ alkyl;

Z is selected from the group consisting of

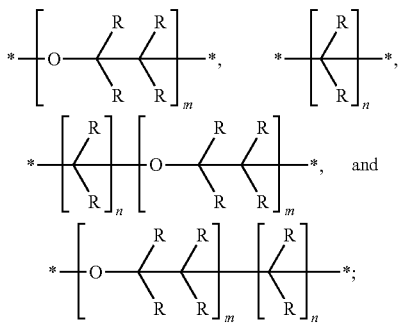

wherein each R is independently selected from —H or a C$_1$ to C$_{10}$ alkyl;
a is an integer from 1 to 5;
b is an integer from 1 to 5;
c is 0 or 1;
d is an integer from 1 to 10;
m is an integer from 1 to 10;
n is an integer from 1 to 10; and
* indicates a point of attachment.

2. The compound of claim 1, wherein R$_f$ is —CF$_3$.
3. The compound of claim 1, wherein R$_f$ is —C$_2$F$_5$.
4. The compound of claim 1, wherein R$_f$ is —CF$_2$CFXCF$_3$ and X is —F.
5. The compound of claim 1, wherein R$_f$ is —CF$_2$CFXCF$_3$ and X is —OC$_3$F$_7$.
6. The compound of claim 1, wherein Z is a single bond, —(CH$_2$)$_n$O—, —OCH$_2$CH$_2$)$_m$O—, or —(CH$_2$)$_n$(OCH$_2$CH$_2$)$_m$O—.
7. The compound of claim 1, wherein Y is H.
8. The compound of claim 1, wherein Y is Cl.
9. The compound of claim 1 wherein Y is Br.
10. The compound of claim 1, wherein R$_x$, R$_y$, and R$_z$ are H.
11. A method for producing compounds of Formula (I)

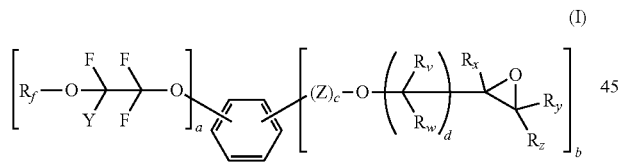

wherein
R$_f$ is —CF$_3$, —C$_2$F$_5$, or —CF$_2$CFXCF$_3$;
X is —F, or —OC$_3$F$_7$;
Y is —H, —Cl, or —Br;
each R is independently, —H, or C$_1$ to C$_{10}$ alkyl;
R$_v$ is —H, or C$_1$ to C$_{10}$ alkyl;
R$_w$ is —H, or C$_1$ to C$_{10}$ alkyl;
R$_x$ is —H, or C$_1$ to C$_{10}$ alkyl;
R$_y$ is —H, or C$_1$ to C$_{10}$ alkyl;
R$_1$ is —H, or C$_1$ to C$_{10}$ alkyl;
Z is selected from the group consisting of

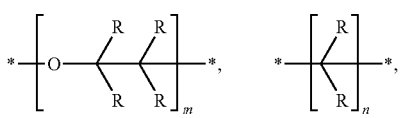

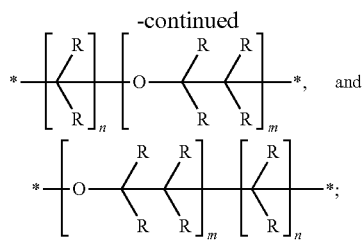

wherein each R is independently selected from —H or a C$_1$ to C$_{10}$ alkyl;
a is an integer from 1 to 5;
b is an integer from 1 to 5;
c is 0 or 1;
d is an integer from 1 to 10;
m is an integer from 1 to 10;
n is an integer from 1 to 10; and
* indicates a point of attachment;
comprising contacting a compound of Formula (XXI)

(XV)

wherein
R$^1$ is —OH, —(CR$_2$)$_n$OH, —(OCR$_2$CR$_2$)$_m$OH, —(CR$_2$)$_n$(OCR$_2$CR$_2$)$_m$OH, —(OCR$_2$CR$_2$)$_m$(CR$_2$)$_n$OH
each R is independently, —H, or C$_1$ to C$_{10}$ alkyl;
a is an integer from 1 to 5;
b is an integer from 1 to 5;
m is an integer from 1 to 10;
n is an integer from 1 to 10
with one or more compounds of formula (XVI)

(XVI)

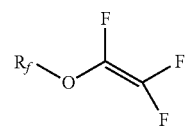

wherein
R$_f$ is —CF$_3$, —C$_2$F$_5$, or —CF$_2$CFXCF$_3$; and
X is —F, or —OC$_3$F$_7$;
in the presence of a base and a solvent having a donatable Y group wherein Y is H, Cl or Br, and
then contacting the resulting product with epichlorohydrin (or substituted epichlorohydrin of formula (XXI)

(XXI)

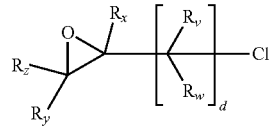

wherein
R$_y$ is —H, or C$_1$ to C$_{10}$ alkyl;
R$_w$ is —H, or C$_1$ to C$_{10}$ alkyl;
R$_x$ is —H, or C$_1$ to C$_{10}$ alkyl;

$R_y$ is —H, or $C_1$ to $C_{10}$ alkyl;

$R_z$ is —H, or $C_1$ to $C_{10}$ alkyl; and d is an integer from 1 to 10 in the presence of an aqueous base in aqueous solution and a catalyst.

12. The method of claim 11, wherein the solvent is tetrahydrofuran, carbon tetrachloride, or carbon tetrabromide.

13. The method of claim 12, wherein the solvent is tetrahydrofuran.

14. The method of claim 11, wherein the base is potassium carbonate, sodium carbonate, or potassium bicarbonate.

15. The method of claim 14, wherein the base is potassium carbonate.

\* \* \* \* \*